Figure 1:
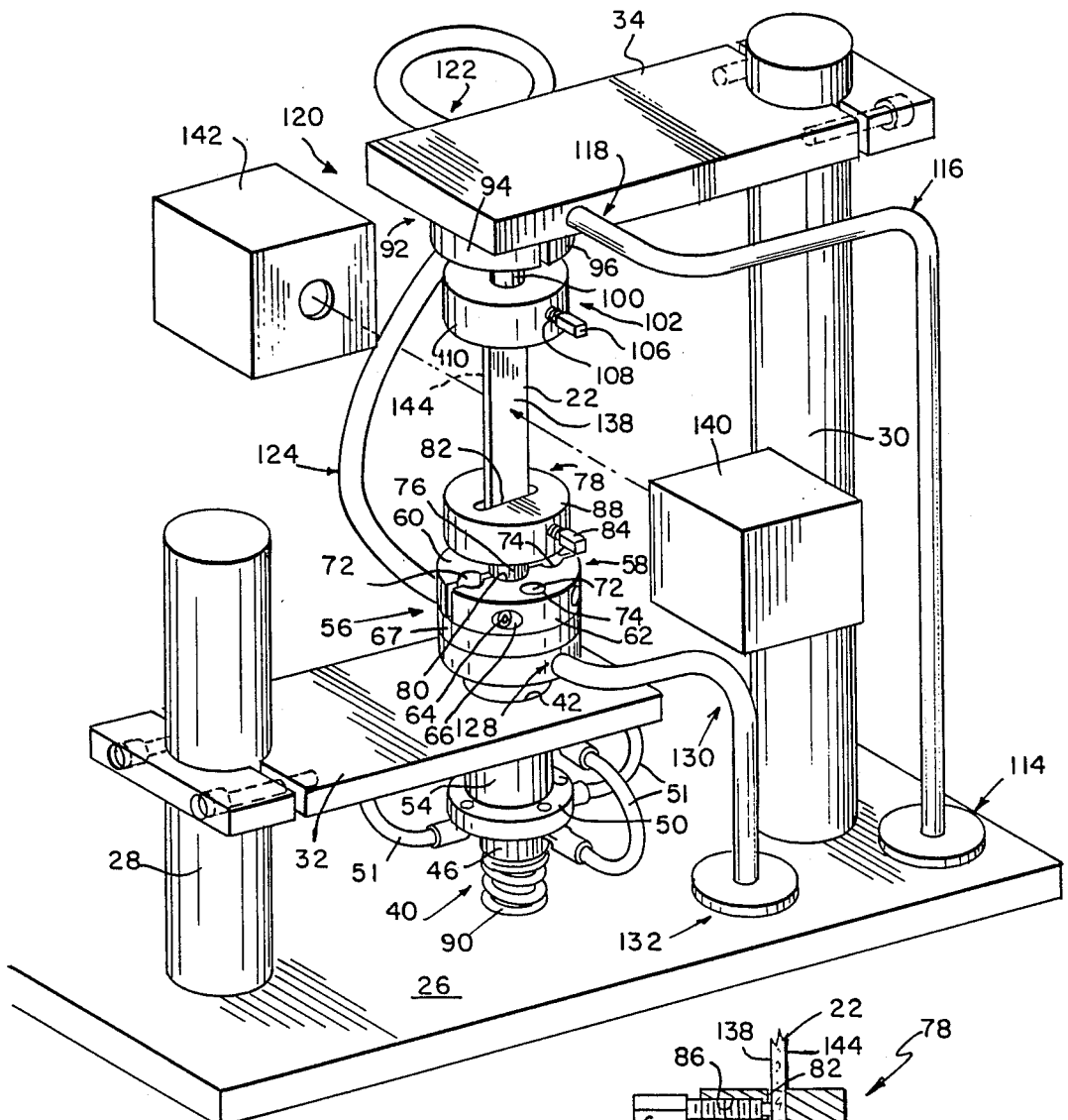

United States Patent [19]

Taylor et al.

[11] Patent Number: 4,865,461

[45] Date of Patent: Sep. 12, 1989

[54] APPARATUS FOR USE IN DETERMINING A THERMAL CHARACTERISTIC OF A SPECIMEN

[75] Inventors: Raymond E. Taylor; Hans Groot, both of West Lafayette; Weldon E. Vaughn, Lafayette, all of Ind.

[73] Assignee: Purdue Research Foundation, West Lafayette, Ind.

[21] Appl. No.: 160,198

[22] Filed: Feb. 25, 1988

[51] Int. Cl.$^4$ .............................................. G01N 25/16
[52] U.S. Cl. ........................................ 374/55; 374/57
[58] Field of Search ..................... 374/44, 55, 56, 57, 374/43, 29, 45; 73/763, 794

[56] References Cited

U.S. PATENT DOCUMENTS

| | | | |
|---|---|---|---|
| 3,433,051 | 3/1969 | Parker | 374/56 |
| 3,680,357 | 8/1972 | Clusener | 374/56 |
| 3,805,589 | 4/1974 | Clusener et al. | 374/56 |
| 3,877,290 | 4/1975 | Cheng | 374/56 |
| 3,919,879 | 11/1975 | Betz | 374/56 |
| 4,313,679 | 2/1982 | Wolff et al. | 374/55 |

*Primary Examiner*—William A. Cuchlinski, Jr.
*Assistant Examiner*—Jeffrey Hohenshell
*Attorney, Agent, or Firm*—Barnes & Thornburg

[57] ABSTRACT

An apparatus for use in determining a thermal characteristic of a specimen includes first and second chucks for engaging two regions of the specimen, a first chuck mounting mechanism for supporting the first chuck in relatively fixed orientation, and a second chuck mounting mechanism. The second chuck mounting mechanism supports the second chuck in relatively movable orientation relative to the first chuck to permit variations in the spacing between the first and second chucks occasioned by thermal variations in the specimen. A base supports the first and second chuck mounting mechanisms. A laser is provided for heating a third region of the specimen lying between the two regions to a different temperature than the two regions. An infrared detector is provided for detecting radiation emitted from the third region. The base, the first chuck mounting mechanism, the first chuck, and the second chuck together comprise a fluid circuit for circulating a fluid through the base, the first chuck mounting mechanism, the first chuck and the second chuck.

11 Claims, 1 Drawing Sheet

APPARATUS FOR USE IN DETERMINING A THERMAL CHARACTERISTIC OF A SPECIMEN

This invention relates to testing of materials to determine their thermal characteristics. The invention is disclosed in the context of testing of the thermal diffusivity at elevated temperatures of high temperature materials such as graphite compositions, so-called superalloys (very high temperature resistant metal alloys), so-called carbon-carbon compositions and the like. However, it is believed that this invention will be useful wherever thermal characteristics of heated or cooled samples are to be tested.

In a typical test system for determining thermal characteristics, such as diffusivity, of heated or cooled samples, samples are mounted in an enclosure, generally referred to as an oven, and heated or cooled to the temperature at which the characteristics are to be measured. This system involving the oven has generally worked well but suffers from one significant drawback. That drawback is generally referred to as thermal inertia. It is the characteristic of ovens that, in order to heat or cool to a particular temperature a sample to be tested, the interior of the oven, the atmosphere within the oven, and all of the test fixturing within the oven must also be at that same temperature. Otherwise, there will be a non-equilibrium condition within the oven and there will be no guarantee that the sample is at its steady state temperature. Heat will flow amoung these various components until steady state conditions are reached in all components. Depending upon where temperature is being measured, at the oven wall, in the atmosphere inside the oven, on the sample-holding fixture, or on the sample itself, the temperature at which the thermal characteristics of the sample are to be measured may or may not have been reached. If it has not been reached, the data obtained will not be meaningful.

There is another related problem, It is that once thermal equilibrium has been reached within the oven and the sample has been tested at the desired temperature, another temperature must ordinarily be reached and other data taken from the sample. The same characteristics of the oven which made thermal equilibrium hard to achieve in the sample before make it hard to reach again. This makes the data collection process in a thermal testing situation time-consuming.

It is an object of the present invention to reduce to the extent presently believed possible the thermal inertia which heretofore characterized thermal testing of samples. It is a further and related object of the present invention to speed up the process of characterizing a thermal test sample at the various temperatures at which it is to be characterized.

According to the invention, an apparatus for use in determining a thermal characteristic of a specimen consists essentially of first and second chucks for engaging two regions of the specimen, a first chuck mounting mechanism for supporting the first chuck in relatively fixed orientation, a second chunk mounting mechanism for supporting the second chunk in relatively moveable orientation relative to the first chuck to permit variations in the spacing between the first and second chunks occasioned by thermal variations in the specimen, and a base for supporting the first and second chuck mounting mechanisms.

Illustratively according to the present invention, the second chunk mounting mechanism comprises a chuck guiding plate defining an aperture, means reciprocable in the aperture back and forth between a first position more closely spaced to the first chuck mounting mechanism and a second position spaced further away from the first chuck mounting mechanism, a spring, and means for mounting the spring between the base and the means reciprocable in the aperture to urge the means reciprocable in the aperture toward the first position.

Additionally according to the present invention, the base, the first chuck mounting means, the first chuck, and the second chuck illustratively together comprise a fluid circuit for circulating a fluid through the base, the first chuck mounting means, the first chuck and the second chunk to aid in controlling the temperature of the first and second chucks.

Illustratively, an apparatus according to the present invention further includes means coupling the two regions of the specimen across two terminals of a current source to aid in controlling the temperature of the specimen.

Figure 2:
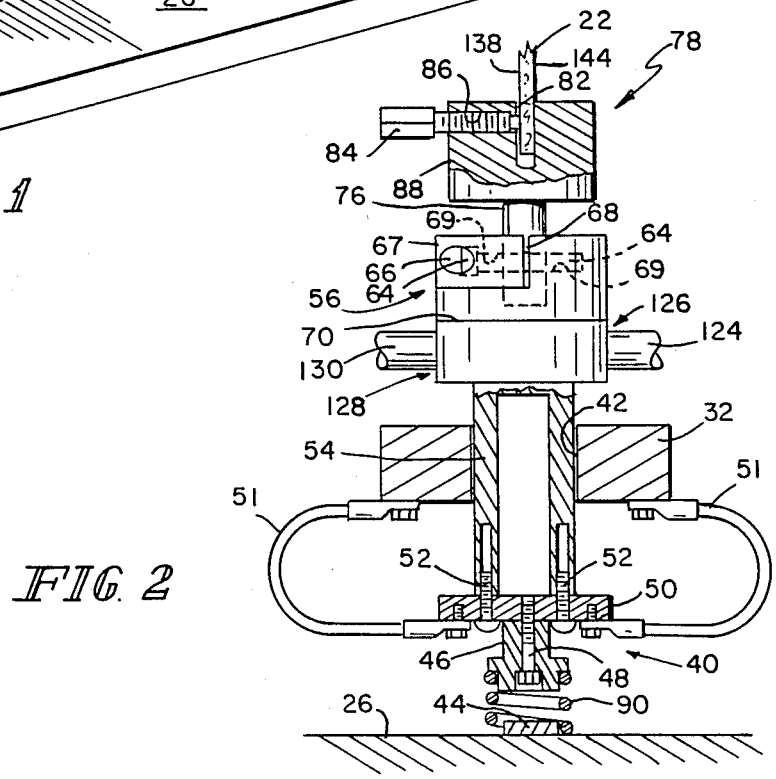

The invention may best be understood by referring to the following description and accompanying drawings which illustrate the invention. In the drawings:

FIG. 1 illustrates a perspective view of apparatus constructed according to the present invention; and FIG. 2 illustrates a fragmentary and partly sectional side elevational view of the apparatus of FIG. 1.

Referring to FIGS. 1-2, a direct hearing apparatus 20 according to the invention is provided for maintaining a sample 22 at a temperature at which a thermal diffusivity test is to be conducted. Illustratively, the sample 22 is a graphite composition, a superalloy, or a carbon-carbon composition formed into a flat rectangular prism-shaped strip. Apparatus 20 includes a mounting base 26, two support posts 28, 30 mounted from, and projecting vertically upward from, base 26 and flat support plates 32, 34 attached in cantilevered support fashion to posts 28, 30, respectively. Plate 32 projects away from post 28 toward post 30. Plate 34 projects away from post 30 toward post 28. Electrical conductors provided within posts 28, 30 are coupled to support plates 32, 34 respectively. Access to these electrical conductors is provided beneath base 26 so that support plates 32, 34 and the apparatus coupled between them can be connected across the terminals of a power supply which is used to heat the sample 22.

A strain relief mechanism 40 is mounted on base 26 and extends upward with sliding clearance through a circular cross-section opening 42 provided in plate 32. Mechanism 40 includes a spring seat 44 mounted on base 26 and centered beneath opening 42. A ceramic stem 46 is attached by a bolt 48 to, and extends downward from, a conductive, illustratively copper, connector plate 50. Electrical conductors 51 are bolted to connector plate 50 and to plate 32 to couple these two together electrically. Connector plate 50 is connected by bolts 52 to the downwardly extending stem 54 of a lower electrode/coolant assembly 56. All electrical connections are insulated from base 26.

A lower sample-holding chuck clamp 58 includes two somewhat D-shaped jaws 60, 62 which are joined together by bolts 64 which extend through countersunk clearance bores 66 in the sidewall 67 of jaw 60 and engage threads in threaded bores 69 in the flat interior face 68 of jaw 62. Jaws 60, 62 are joined to the top surface 70 of lower electrode/coolant assembly 56 by bolts 72 which extend through countersunk unthreaded bores 74 in jaws 60, 62 and into threaded bores in lower electrode/coolant assembly 56. Bores 74 are large enough in diameter to permit the clamping/unclamping movement of the downwardly extending stem 76 of a lower sample-holding chuck 78. Stem 76 is insertable into a generally circular cross-section opening 80 defined between jaws 60, 62 to clamp stem 76 in response to tightening of bolts 64. An upwardly opening slot 82 in chuck 78 has a configuration and a cross-sectional area just slightly larger than the configuration and cross sectional area of the lower end of sample 22. A bolt 84 extends through a threaded bore 86 in the sidewall 88 of chuck 78. Bore 86 intersects slot 82, permitting bolt 84 to engage the lower end of sample 22 which is inserted in slot 82. A coil spring 90 retained between spring seat 44 and the lower end of stem 46 biases strain relief mechanism 40 upward in opening 42.

An upper sample-holding chuck clamp 92 includes two somewhat D-shaped jaws 94, 96 which are joined together and to the underside of plate 34 in the same manner as was chuck clamp 58. A generally circular cross-section opening defined between jaws 94, 96 is large enough in diameter to permit the clamping and unclamping of the upwardly extending stem 100 of an upper sample-holding chuck 102. A downwardly opening slot (not shown) in chuck 102 has a configuration and a cross sectional area just slightly larger than the configuration and cross sectional area of the upper end of sample 22. A bolt 106 extends through a threaded bore 108 in the sidewall 110 of chuck 102. Bore 108 intersects the upper sample-holding slot, permitting bolt 106 to engage the upper end of sample 22 which is inserted into the upper sample-holding slot.

A cooling system is provided to prevent overheating of the various components of th apparatus 20 as a current is being passed through the conductors within posts 28, 30, the support plates 32, 34, and the apparatus which couples them together electrically. The cooling system comprises an inlet 114 in base 26 or cooling water. A flexible conduit 116 extends upward from inlet 114 to an inlet 118 into upper plate 34. A cooling pathway (not shown) is provided within plate 34 at least in the region where jaws 94, 96 are attached to it. This cooling pathway terminates at an outlet 122 from which cooling water flows through a flexible conduit 124 downward to an inlet 126 into lower electrode/coolant assembly 56. A cooling pathway (not shown) is also provided through assembly 56, terminating at an outlet 128 from which cooling water flows through a flexible conduit 130 to a cooling water outlet 132.

In use, a sample 22 whose thermal diffusivity as a function of its temperature is to be ascertained is mounted in the chucks 78, 102. Typically an electrical current and a cooling fluid, such as water, are passed through their respective circuits in the apparatus 20. The sample 22 is heated to a steady state condition at the temperature at which its thermal diffusivity is to be ascertained. Then additional heat is applied to one side of the sample 22 and the temperature of the other side of the sample 22 is monitored to determine how long a time expires before heat applied on one side becomes detectable on the other side. The techniques for applying heat to one side of the sample 22 and detecting the diffusion of the applied heat through the sample 22 to the other side are well known. These techniques can include, for example, flooding one side 138 of the sample 22 with laser light from a laser 140 and monitoring the output from an infrared detector 142 mounted in such a fashion that it can view the unexposed side 144 of the sample 22.

What is claim is:

1. An apparatus for use in determining a thermal characteristic of a specimen, the apparatus consisting essentially of first and second chunks for engaging two regions of the specimen, a first chuck mounting mechanism for supporting the first chunk in relatively fixed orientation, a second chuck mounting mechanism for supporting the second chuck in relatively movable orientation relative to the first chuck to permit variations in the spacing between the first and second chucks occasioned by thermal variations in the specimen, and a base for supporting the first and second chuck mounting mechanisms, the second chuck mounting mechanism comprising a chuck guiding plate defining an aperture, means reciprocable in the aperture back and fourth between a first position more closely spaced to the first chuck mounting mechanism and a second position spaced further away from the first chuck mounting mechanism, a spring, and means for mounting the spring between the base and the means reciprocable in the aperture to urge the means reciprocable in the aperture toward the first position.

2. The apparatus of claim 1 wherein the base, the first chuck mounting means, the first chuck, and the second chuck together comprise a fluid circuit for circulating a fluid through the base, the first chuck mounting means, the first chuck and the second chuck.

3. The apparatus of claim 2 including means for coupling the two regions of the specimen across two terminals of a current source.

4. The apparatus of claim 1 including means for coupling the two regions of the specimen across two terminals of a current source.

5. An apparatus for use in determining a thermal characteristic of a specimen, the apparatus consisting essentially of first and second chucks for engaging two regions of the specimen, a first chuck mounting mechanism for supporting the first chuck in relatively fixed orientation, a second chuck mounting mechanism for supporting the second chuck in relatively movable orientation relative to the first chuck to permit variations in the spacing between the first and second chucks occasioned by thermal variations in the specimen, and a base for supporting the first and second chuck mounting mechanisms, the base, the first chuck mounting means, the first chuck, and the second chuck together comprising a fluid circuit for circulating a fluid through the base, the first chuck mounting means, the first chuck and the second chuck.

6. The apparatus of claim 5 including means for coupling the two regions of the specimen across two terminals of a current source.

7. An apparatus for use in determining a thermal characteristic of a specimen, the apparatus consisting essentially of first and second chucks for engaging two regions of the specimen, a first chuck mounting mechanism for supporting the first chuck in relatively fixed orientation, a second chuck mounting mechanism for supporting the second chuck in relatively movable orientation relative to the first chuck to permit variations in the spacing between the first and second chucks occasioned by thermal variations in the specimen, a base for supporting the first and second chuck mounting mechanisms, means for heating a third region of the specimen to a different temperature than the two regions, the third region lying between the two regions, and means for detecting radiation emitted from the third region, the second chuck mounting mechanism comprising a chuck guiding plate defining an aperture, means reciprocable in the aperture back and forth between a first position more closely spaced to the first chuck mounting mechanism and a second position spaced further away from the first chuck mounting mechanism, a spring, and means for mounting the spring between the base and the means reciprocable in the aperture to urge the means reciprocable in the aperture toward the first position.

8. The apparatus of claim 7 wherein the base, the first chuck mounting means, the first chuck, and the second chuck together comprise a fluid circuit for circulating a fluid through the base, the first chuck mounting means, the first chuck and the second chuck.

9. The apparatus of claim 8 including means for coupling the two regions of the specimen across two terminals of a current source.

10. An apparatus for use in determining a thermal characteristic of a specimen, the apparatus consisting essentially of first and second chucks for engaging two regions of the specimen, a first chuck mounting mechanism for supporting the first chuck in relatively fixed orientation, a second chuck mounting mechanism for supporting the second chuck in relatively movable orientation relative to the first chuck to permit variations in the spacing between the first and second chucks occasioned by thermal variations in the specimen, a base for supporting the first and second chuck mounting mechanisms, means for heating a third region of the specimen to a different temperature than the two regions, the third region lying between the two regions, and means for detecting radiation emitted from the third region, the base, the first chuck mounting means, the first chuck, and the second chuck together comprising a fluid circuit for circulating a fluid through the base, the first chuck mounting means, the first chuck and the second chuck.

11. The apparatus of claim 10 including means for coupling the two regions of the specimen across two terminals of a current source.

* * * * *